United States Patent
Bhagwan et al.

(10) Patent No.: US 11,043,291 B2
(45) Date of Patent: Jun. 22, 2021

(54) STREAM BASED NAMED ENTITY RECOGNITION

(71) Applicant: INTERNATIONAL BUSINESS MACHINES CORPORATION, Armonk, NY (US)

(72) Inventors: Varun Bhagwan, San Jose, CA (US); Clemens Drews, San Jose, CA (US); Daniel F. Gruhl, San Jose, CA (US); Neal R. Lewis, San Jose, CA (US); April L. Webster, Mountain View, CA (US); Steven R. Welch, Gilroy, CA (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 680 days.

(21) Appl. No.: 14/291,189

(22) Filed: May 30, 2014

(65) Prior Publication Data
US 2015/0347433 A1    Dec. 3, 2015

(51) Int. Cl.
*G16H 15/00*     (2018.01)
*G06F 16/36*     (2019.01)
(Continued)

(52) U.S. Cl.
CPC ........... *G16H 15/00* (2018.01); *G06F 16/374* (2019.01); *G06F 19/00* (2013.01); *G16H 10/60* (2018.01)

(58) Field of Classification Search
CPC ............. G06F 21/6218; G06F 21/6227; G06F 17/30737; G06F 19/324; G06F 19/3487;
(Continued)

(56) References Cited

U.S. PATENT DOCUMENTS 6,915,254 B1 * 7/2005 Heinze ................... G06F 40/20
                                                          704/9
7,558,778 B2    7/2009 Carus et al.
(Continued)

OTHER PUBLICATIONS

Yu et al., "A Short Introduction to MiniNLP", Department of Biostatistics, Harvard School of Public Health, Nov. 23, 2013 (Year: 2013).*
(Continued)

*Primary Examiner* — Tony Mahmoudi
*Assistant Examiner* — Michael Le
(74) *Attorney, Agent, or Firm* — Erik Huestis; Stephen Kenny; Foley Hoag LLP

(57) ABSTRACT

Embodiments of the present invention relate to performing entity recognition on a stream while providing ongoing training or supplementation of an entity dictionary. In one embodiment, a method of and computer program product for stream based named entity recognition is provided. A first portion of a textual input is received. A plurality of patterns is applied to the first portion to determine that a predetermined type is present in the first portion. Approval is requested of the presence of the predetermined type. An indication of approval or disapproval of the predetermined type is received. A dictionary is supplemented according to the indication. A second portion of the textual input is received. The plurality of patterns is applied to the second portion.

20 Claims, 3 Drawing Sheets

(51) Int. Cl.
*G16H 10/60* (2018.01)
*G06F 19/00* (2018.01)

(58) Field of Classification Search
CPC ........ G06F 16/374; G06F 10/60; G06F 15/00; G06Q 10/10
USPC ....................................................... 707/783
See application file for complete search history.

(56) References Cited

U.S. PATENT DOCUMENTS

| | | | | |
|---|---|---|---|---|
| 7,610,192 | B1* | 10/2009 | Jamieson | G06Q 40/08 704/9 |
| 7,657,521 | B2 | 2/2010 | Masarie et al. | |
| 7,979,288 | B2 | 7/2011 | Wilkinson et al. | |
| 8,260,779 | B2 | 9/2012 | Hudgins et al. | |
| 8,321,277 | B2* | 11/2012 | Coulomb | G06Q 30/0603 704/270.1 |
| 2003/0154208 | A1* | 8/2003 | Maimon | G06F 19/324 |
| 2005/0065776 | A1* | 3/2005 | Coden | G06F 17/278 704/10 |
| 2005/0240439 | A1* | 10/2005 | Covit | G16H 15/00 705/2 |
| 2006/0173715 | A1* | 8/2006 | Wang | G06Q 10/10 705/2 |
| 2006/0261145 | A1* | 11/2006 | Robertson | G16H 10/60 235/375 |
| 2008/0275732 | A1* | 11/2008 | Falchuk | G06Q 10/00 705/3 |
| 2009/0204596 | A1* | 8/2009 | Brun | G06F 17/278 |
| 2009/0281837 | A1* | 11/2009 | Li | G16H 70/60 705/3 |
| 2009/0299977 | A1* | 12/2009 | Rosales | G06F 16/24573 |
| 2010/0063799 | A1* | 3/2010 | Jamieson | G06F 16/36 704/9 |
| 2011/0307435 | A1* | 12/2011 | Overell | G06N 20/00 706/46 |
| 2012/0158432 | A1* | 6/2012 | Jain | G16H 15/00 705/3 |
| 2012/0296932 | A1 | 11/2012 | Bao et al. | |
| 2013/0030854 | A1* | 1/2013 | McCormack | H04L 51/28 705/7.14 |
| 2013/0060793 | A1* | 3/2013 | Bandyopadhyay | G16H 10/60 707/755 |
| 2013/0086096 | A1 | 4/2013 | Koshimizu et al. | |
| 2013/0110823 | A1* | 5/2013 | Su | G06F 17/30867 707/723 |
| 2013/0124523 | A1 | 5/2013 | Rogers et al. | |
| 2014/0379386 | A1* | 12/2014 | Drennan, III | G06F 16/2465 705/4 |

OTHER PUBLICATIONS

Savova et al., "Mayo Clinical Text Analysis and Knowledge Extraction System (cTAKES): architecture, component, evaluation and applications", J Am Med Inform Association 2010; 17:507-513, 7 pages printed (Year: 2010).*

Meystre et al., "Extracting Information from Textual Documents in the Electronic Health Record: A review of Recent Research", IMIA Yearbook of Medical Informatics, 2008, 17 pages printed (Year: 2008).*

Denecke, Kerstin, "Extracting Medical Concepts from Medical Social Media with Clinical NLP Tools: A Qualitative Study", University of Leipzig, 7 pages printed, Date taken from PDF properties (Year: 2014).*

Tsuruoka, Y. et al. (Jul. 2011). Discovering and visualizing indirect associations between biomedical concepts. Bioinformatics (Oxford, England), vol. 27, No. 13, pp. i111-i119: See sections 2 & 3.

Erhardt, R. A. et al. (Apr. 2006). Status of text-mining techniques applied to biomedical text. Drug Discovery Today, vol. 11, No. 7/8: See pp. 319-321.

* cited by examiner

STREAM BASED NAMED ENTITY RECOGNITION

BACKGROUND

Embodiments of the present invention relate to stream based named entity recognition, and more specifically, performing entity recognition on a stream while providing ongoing training or supplementation of an entity dictionary.

BRIEF SUMMARY

According to one embodiment of the present invention, a method of and computer program product for stream based named entity recognition are provided. A first portion of a textual input is received. A plurality of patterns is applied to the first portion to determine that a predetermined type is present in the first portion. Approval is requested of the presence of the predetermined type. An indication of approval or disapproval of the predetermined type is received. A dictionary is supplemented according to the indication. A second portion of the textual input is received. The plurality of patterns is applied to the second portion.

DETAILED DESCRIPTION

Named-entity recognition (NER) is the process of locating and classifying elements from text into predefined categories. Examples of categories that may be of interest include persons, organizations, locations, expressions of times, quantities, monetary values, percentages, countries, pharmaceuticals, equipment, brand names, and sports. A NER algorithm may be, e.g., grammar based or based on a statistical model. One example of a NER algorithm is the Glimpse algorithm, disclosed in commonly invented and assigned patents applications. NER algorithms may be applicable to various use cases, including those that involve identification of text containing certain categories of terms or concepts and those that involve linking entities in a source text to context appropriate information.

Various machine learning techniques may be applied to NER. However, a NER system that has been trained on data from one domain tends not to provide high quality results in other evolving domains. That is, a trained classifier tends to be brittle. Accordingly, in order to obtain reliable results, a NER system intended for handling of domain-specific data, such as clinical data, for example, should generally be trained on such clinical data.

NER algorithms may be run on static data sets, both for training and for recognition of entities. For example, a NER algorithm may be run periodically against a static data set in order to update the entity information related for that static data set. Using this process, a dictionary of entities may be built up based on the input data set. However, running training and recognition processes against static data sets is inflexible.

According to various embodiments of the present disclosure, systems, methods and computer program products are provided for application of NER over real-time streamed natural language. Detection of potential entities in real time as data is entered is advantageous both for classification and for training of the NER algorithm. Applying a pattern-based NER algorithm to real-time streaming clinical data allows instantaneous identification of new clinical concepts and terms, as well as possible false positives by the NER algorithm. Such a mechanism provides a feedback loop for optimizing an NER algorithm, thereby providing incremental training. In addition, a dictionary of new entities may be incrementally augmented based terms recognized by the NER algorithm.

Figure 1:
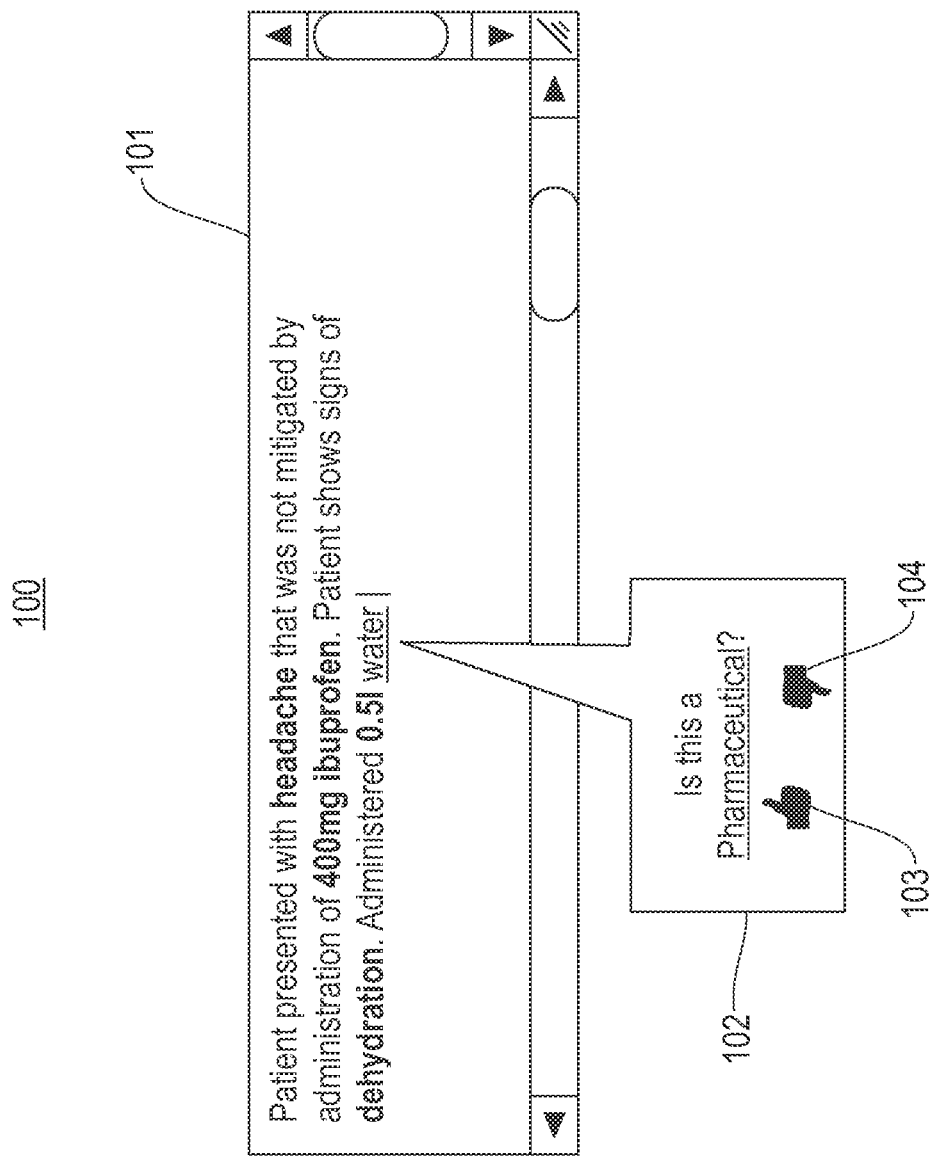
FIG. 1 depicts an exemplary user interface according to an embodiment of the present disclosure.

Referring to FIG. 1, an exemplary user interface according to an embodiment of the present disclosure is provided. User interface 100 includes text entry region 101. Text entry region 101 may be integrated into existing software, for example electronic health records systems. The look and feel of user interface 100 may vary based upon the platform and software used to provide the user interface, and the layout provided in FIG. 1 is merely exemplary. As text is entered into text entry region 101, a NER algorithm is applied. In this exemplary embodiment, recognized entities are bolded. However, alternative visual indicators may be adopted, such as color coding by entity type.

As a user (e.g., a doctor) types into input region 101, the input stream is check against a previously generated pattern set, looking for possible clinical data concepts, such as pharmaceuticals, family history, or medical procedures. If a potential clinical entity is detected immediately after being typed in, the term is identified for later adjudication (e.g., by highlighting) by the doctor via a user interface. In some embodiment, an immediate user interface element is displayed, such as popup 102. Popup 102 displays a tentative type identification, and requests feedback from the user by clicking either button 103 or 104 according to whether the user agrees with the automated type determination. In other embodiments, the list of entities is retained for later review and the user is not prompted during text entry. For example, the user may be queried to confirm each entity contained in the input text one at a time after the completion of text entry. In some embodiments, confirmation of only a subset of entities is requested of a user. In such embodiments, a random subset may be selected for review. Alternatively, entities that are recognized with less than a predetermined degree of confidence may be selected for review. In yet other embodiments, a predetermined number of entities may be selected for review, the selected entities having the lowest confidence of the entities in the input text.

A variety of entity types may be recognized in various embodiments of the present disclosure. In the example of FIG. 1, "headache" and "dehydration" are recognized as clinical conditions; "400 mg" and "0.51" are recognized as quantities; and "Ibuprofen" is recognized as a pharmaceutical.

In some embodiments, complete entity recognition may require that an minimum amount of text be entered prior to entity recognition. For example, NER algorithms that are pattern based may require that an entire sentence be entered in order to apply patterns. Accordingly, in some embodiments entity recognition is performed once an entire text is entered by a user. In other embodiments, a sentence detector is applied to text as it is entered, and NER is performed once each sentence of the input concludes.

Stream based named entity recognition according to embodiments of the present disclosure provides immediate, real-time, high precision structured data from dynamic unstructured sources. This data is useful, for example, in cost modeling and risk analysis. For example, by obtaining more accurate information about what pharmaceuticals its patients are taking, a hospital can more accurately model for future costs and risks. It also helps validate clinician authored information to assure accurate use of terminology. In addition, this data may be used to detect the presence of new entities for inclusion in a dictionary. For example, a newly released pharmaceutical may not be present in existing dictionaries, but may be recognized as a pharmaceutical based on its context and then stored in a dictionary.

Various NER algorithms may be used according to various embodiments of the present disclosure. Among these are pattern-based NER algorithms. Some suitable algorithms are domain-specific, for example being targeted to clinical concepts. One example of a pattern based clinical concept NER algorithm is Glimpse, which is disclosed in commonly invented and assigned patent applications. It is advantageous in many use cases for the NER algorithm selected to be tuned to the particular domain in which it is to be applied. For example, certain natural language patterns arise in clinical records that a general purpose NER algorithm may not be suited to. However, a general purpose NER algorithm may be used according to various embodiments of the present disclosure.

As noted above, a pattern-based NER algorithm such as Spot may be applied to a stream S of text. In general, a pattern-based NER algorithm may identify a given concept or entity type where a set of left and right side patterns L and R are matched by the input text. For example, a left hand pattern of "administer(ed?) \d+\H*" may be associated with the clinical concept of pharmaceuticals. The right hand pattern of "mg" may be associated with quantities. In these cases, the NER algorithm would recognize "water" as a pharmaceutical and "400 mg" as a quantity, as depicted in FIG. 1. Although the above examples are phrased as regular expressions, no particular syntax is required for the practice of the systems and methods of the present disclosure.

In some embodiments, a tentative concept or entity type is subject to additional post-processing. For example, an additional predetermined dictionary may be applied to vet the entity type.

In some embodiments, the system is seeded with a pattern set for entities of interest. The seed set may be generated by an initial run of a NER algorithm in a supervised, unsupervised, or semi-supervised mode. After a seed set is created, the patterns and dictionary are used in and refined by the real time system as described above.

In addition to user validation as text is entered, the systems and methods of the present disclosure may be used to perform batch review and training on an existing corpus of data. In such embodiments, the corpus of data is read seriatim and processed by the NER algorithm as reading progresses. A user is queried as the stream is read to validate the entity types of each identified entity. This enables efficient learning over an existing corpus, as subsequent portions of the corpus will benefit from the training performed on precedent portions.

In some embodiments, the systems and methods of the present disclosure are applied to third party data streams, such as microblogging services or newsfeeds. In such embodiments, existing patterns are applied to the data stream as it is read. New entities may be recognized in the data stream and stored for later review, or immediately brought to the attention of a user. For example, an existing pattern that identifies names of dog breeds may be applied to microblogging services for early identification of new breed names. These new names may be used to supplement a dictionary of dog breeds, or to alert a user or subscriber to the reference to such a new breed. A variety of alert methodologies known in the art may be used to bring a user's attention to a new item of interest, such as text alerts, microblogging messages, audible chimes, or on screen notifications. Validation of the new term may be requested of a subject matter expert or other user.

In some embodiments, a client-side application is provided that contains a dictionary and a set of patterns. Such a client-side application reads text from a stream as described above, and locally applies a NER algorithm. In other embodiments, a server application performs these functions, and provides output to a user via a web interface, email, text message, or other user interface mechanism known in the art.

Figure 2:
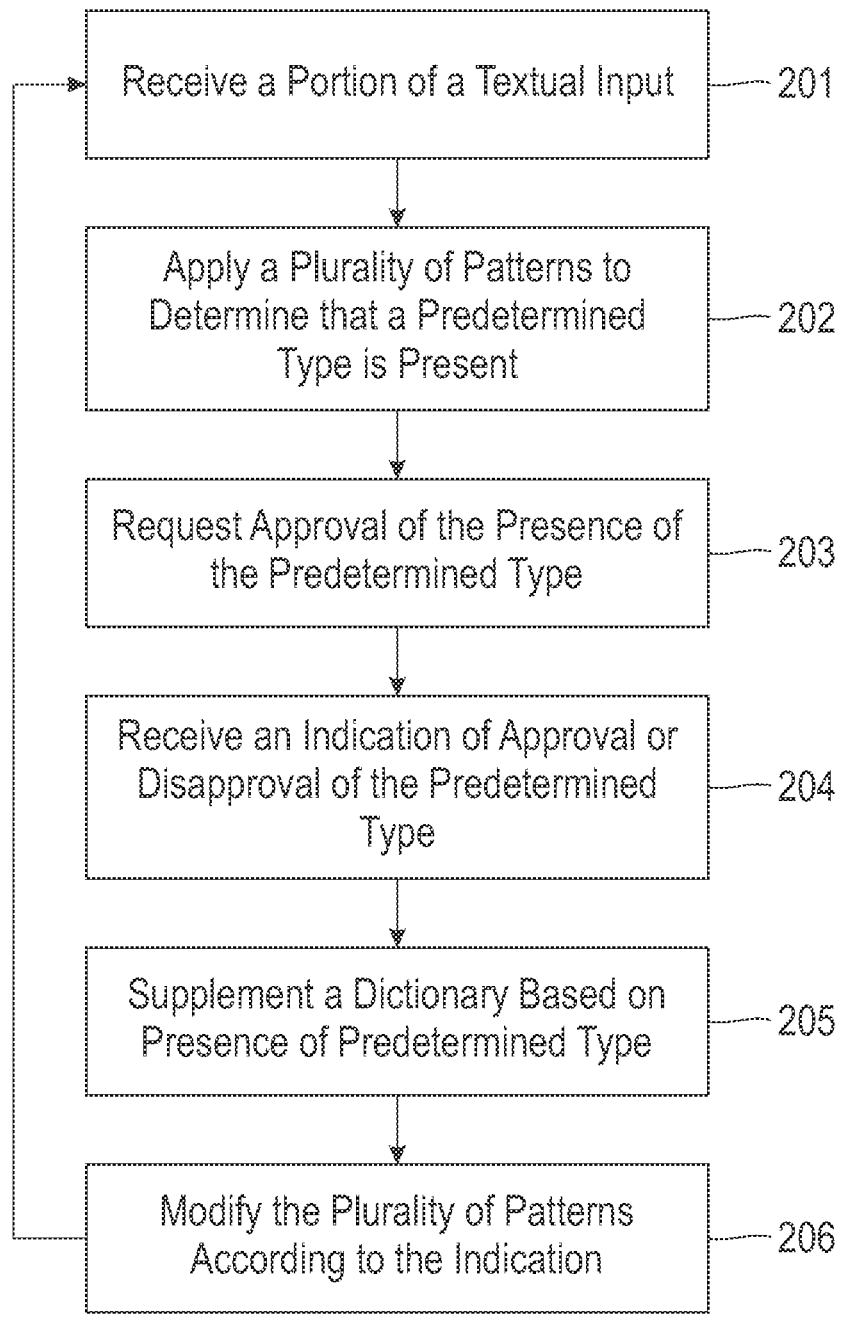
FIG. 2 depicts a method for stream based entity recognition according to embodiments of the present disclosure.

Referring now to FIG. 2, a method a method for stream based entity recognition according to embodiments of the present disclosure is depicted. A portion of a textual input is received 201. In some embodiments, the textual input is a text stream. In some embodiments, the text originates from a static file. In some embodiments, the text originates from a microblogging service. In some embodiments, the text originates from user input. A plurality of patterns is applied to determine whether a predetermined type is present 202. In alternative embodiments, a non-pattern based NER algorithm is applied instead. The predetermined type may express a given concept (such as the clinical concept of a pharmaceutical) or other type (such as quantity, person, or place). The detection of a type may be tied to any subsequence of the tokens of the input text. In some embodiments, the subsequence is a word in a sentence. For example, a given name may generally be a single word in an input stream. Once a determination is made that a given type is present, approval is sought. In some embodiments, the approval is sought of a user in real time. In other embodiments, approval is deferred until an entire textual input or a predetermined subset thereof is processed. The presence of a detected type may be approved or disapproved 204. This approval may come from a user or subject matter expert in real time who may be local or remote. In alternative embodiments, the approval is deferred and received from a user after processing of the textual input. In some embodiments, the approval comes from a second system, for example a complementary NER algorithm running on the same or another computer system. In some embodiment, a dictionary is supplemented based on the presence of the predetermined type 205. For example, once approval is obtained, an approved term may be added to a dictionary of like terms. In some embodiments, the patterns are modified based on the detected type 206. For example, in a trainable pattern-based NER, the set of patterns may be modified based on the context of a newly detected term. In general, the approval or disapproval of a detection may be used as a training step for alternative NER algorithms or other trainable classifiers.

In some embodiments, steps 205 and 206 are performed concurrently. In other embodiments, steps 205 and 206 are performed in reverse order. In particular, supplementation of the dictionary may be independent from modification of the patterns, and may be executed in any order. Thus, in some embodiments, step 205 may also be deferred indefinitely. In such embodiments, dictionary supplementation is performed as a batch after a predetermined period of time, after a predetermined number of entries have been compiled, or upon initiation by a user.

Figure 3:
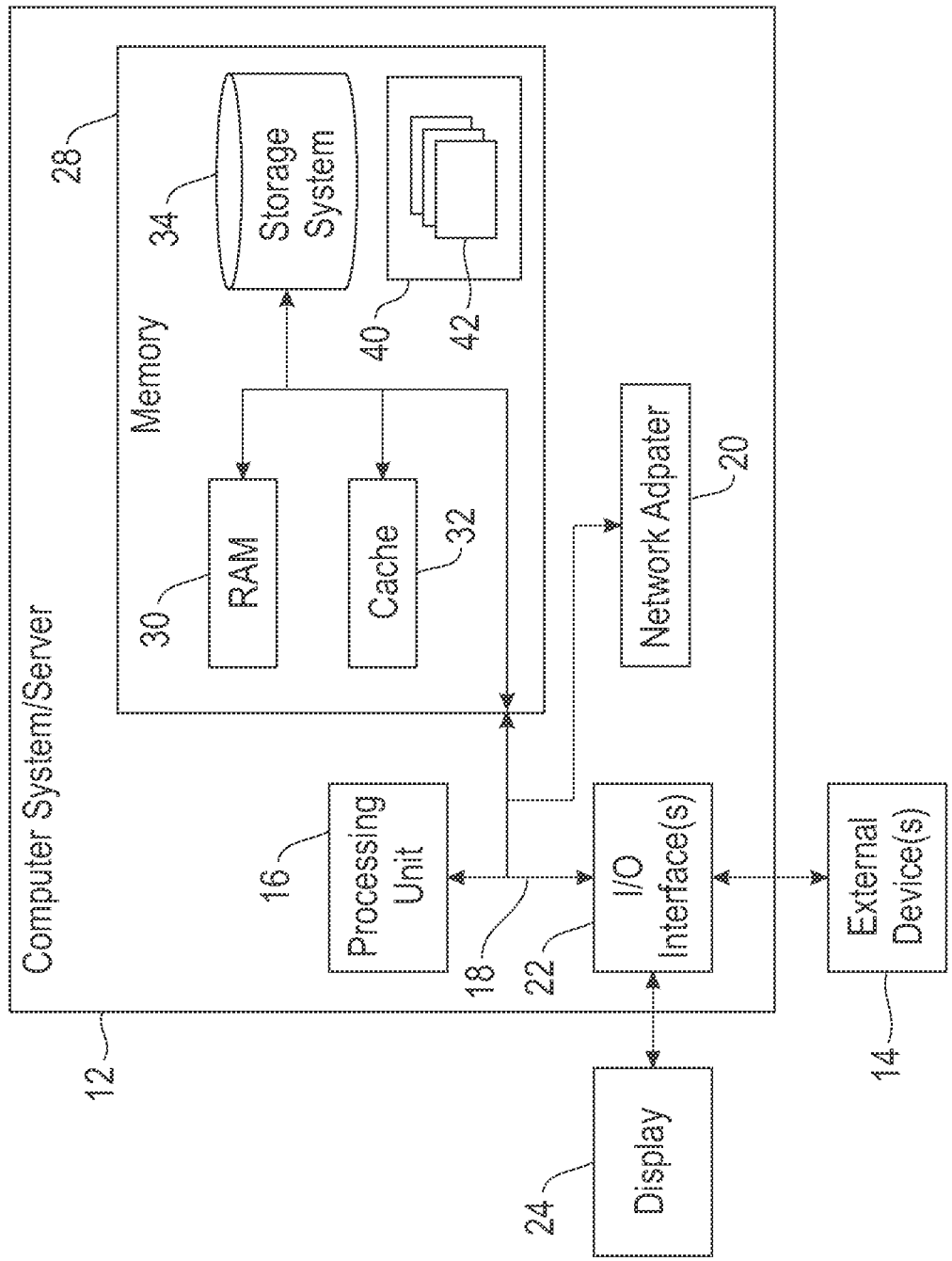
FIG. 3 depicts a computing node according to an embodiment of the present invention.

Referring now to FIG. 3, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   receiving a first portion of a textual input;
   applying a first search pattern and a second search pattern to the first portion, wherein the first search pattern is one of a first plurality of search patterns and each of the first plurality of search patterns is assigned a clinical concept, the second search pattern is one of a second plurality of search patterns and each of the second plurality of search patterns is assigned a quantity, each of the first and second search patterns comprising a plurality of tokens and at least one regular expression operator, and wherein applying the first search pattern and the second search pattern comprises:
      dividing the first portion into left, right, and middle subsets, the left subset adjacent to and appearing before the middle subset within the textual input, and the middle subset adjacent to and appearing before the right subset within the textual input,
      matching the left subset to the first search pattern, and matching the middle subset to the second search pattern;

assigning the clinical concept assigned to the first search pattern to the right subset;

extracting the middle subset corresponding to the quantity;

requesting approval of the presence of the assigned clinical concept in the right subset, the right subset comprising a term;

receiving an indication of approval or disapproval of the clinical concept;

supplementing a dictionary with the term according to the indication;

modifying the first and second pluralities of search patterns according to the indication and a term context indicated by the left and middle subsets;

receiving a second portion of the textual input; and applying the modified first and second pluralities of search patterns to the second portion.

2. The method of claim 1, wherein the textual input is a stream.

3. The method of claim 1, wherein the first portion is received from a user.

4. The method of claim 3, wherein requesting approval comprises:

prompting the user for the indication.

5. The method of claim 4, wherein prompting the user comprises:

displaying a prompt on a digital display.

6. The method of claim 1, wherein the first portion is received from a source selected from the group consisting of:

a newsfeed; and a microblogging service.

7. The method of claim 1, wherein the term comprises a word.

8. The method of claim 7, further comprising:

storing the right subset; and storing at least one additional word, wherein supplementing the dictionary comprises:

adding the right subset and the at least one additional word to the dictionary.

9. The method of claim 1, wherein requesting approval comprises displaying the right subset to a user.

10. The method of claim 1, wherein the textual input is a predetermined subset of a stream.

11. The method of claim 10, wherein requesting approval of the presence of the clinical concept comprises:

adding a request to a queue of requests.

12. The method of claim 11, wherein the queue of requests is provided to a user at a predetermined time.

13. The method of claim 1, wherein requesting approval and receiving a second portion occur substantially concurrently.

14. The method of claim 1, wherein at least one search pattern of the first plurality of search patterns and the second plurality of search patterns comprises a non-alphanumeric symbol.

15. A computer program product for stream-based named entity recognition, the computer program product comprising a computer readable storage medium having program instructions embodied therewith, the program instructions executable by a processor to cause the processor to perform a method comprising:

receiving a first portion of a textual input;

applying a first search pattern and a second search pattern to the first portion, wherein the first search pattern is one of a first plurality of search patterns and each of the first plurality of search patterns is assigned a clinical concept, the second search pattern is one of a second plurality of search patterns and each of the second plurality of search patterns is assigned a quantity, each of the first and second search patterns comprising a plurality of tokens and at least one regular expression operator, and wherein applying the the first search pattern and the second search pattern comprises:

dividing the first portion into left, right, and middle subsets, the left subset adjacent to and appearing before the middle subset within the textual input, and the middle subset adjacent to and appearing before the right subset within the textual input, matching the left subset to the first search pattern, and matching the middle subset to the second search pattern;

assigning the clinical concept assigned to the first search pattern to the right subset;

extracting the middle subset corresponding to the quantity;

requesting approval of the presence of the assigned clinical concept in the right subset, the right subset comprising a term;

receiving an indication of approval or disapproval of the clinical concept;

supplementing a dictionary with the term according to the indication;

modifying the first and second pluralities of search patterns according to the indication and a term context indicated by the left and middle subsets;

receiving a second portion of the textual input; and applying the modified first and second pluralities of search patterns to the second portion.

16. The computer program product of claim 15, wherein the textual input is a stream.

17. The computer program product of claim 15, wherein the first portion is received from a user.

18. The computer program product of claim 17, wherein requesting approval comprises:

prompting the user for the indication.

19. The computer program product of claim 18, wherein prompting the user comprises:

displaying a prompt on a digital display.

20. The computer program product of claim 15, wherein at least one search pattern of the first plurality of search patterns and the second plurality of search patterns comprises a non-alphanumeric symbol.

* * * * *